United States Patent [19]

Santangelo et al.

[11] Patent Number: 5,438,047
[45] Date of Patent: Aug. 1, 1995

[54] DIPHOSPHATES OF CATECHOLAMINES AND PHARMACEUTICAL COMPOSITIONS CONTAINING THEM

[75] Inventors: Francesco Santangelo, Milan; Cesare Casagrande, Arese; Gabriele Norcini, Maddalena Somma Campagna, all of Italy

[73] Assignee: Zambon Group S.p.A., Vicenza, Italy

[21] Appl. No.: 204,394

[22] Filed: Mar. 28, 1994

[30] Foreign Application Priority Data

Jul. 30, 1992 [IT] Italy ................. MI92A1855

[51] Int. Cl.$^6$ ................. C07F 9/12; A61K 31/66
[52] U.S. Cl. ................. 514/104; 558/162
[58] Field of Search ................. 514/104; 558/162

[56] References Cited

U.S. PATENT DOCUMENTS 3,132,171 5/1964 Plaut .
4,618,484 10/1986 Pawelek ................. 514/107 X
4,673,671 6/1987 Casagrande et al. .

*Primary Examiner*—Robert W. Ramsuer
*Assistant Examiner*—Michael G. Ambrose
*Attorney, Agent, or Firm*—Stevens, Davis, Miller & Mosher

[57] ABSTRACT

Diphosphates of catecholamines having formula (I) wherein R, $R_1$, $R_2$, $R_3$, $R_4$, $R_5$, $R_6$, $R_7$ and X have the meanings reported in the description, are useful in the therapy of cardiovascular and renal diseases.

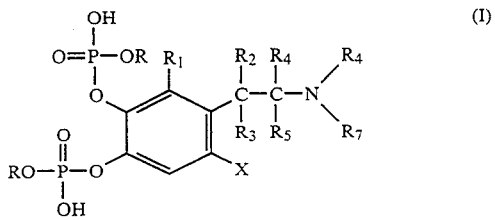

4 Claims, No Drawings

DIPHOSPHATES OF CATECHOLAMINES AND PHARMACEUTICAL COMPOSITIONS CONTAINING THEM

This application was filed under 35 U.S.C. § 371 and is based upon International Application No. PCT/EP93/01927 which has an international filing date of Jul. 21, 1993.

DESCRIPTION

The present invention relates to the diphosphates of catecholamines, a process for their preparation and pharmaceutical compositions containing them.

In European patent No. 0 167 204 (SIMES Società Italiana Medicinali e Sintetici S.p.A.) is described a method for improving the absorption and the effectiveness of the catecholamines consisting in the conversion of such intermediates in monophosphorylated derivatives. Furthermore it is known that the phosphorylation of the catecholamines leads to the formation of monophosphorylation products on one of the two catechol hydroxy groups, using also an excess of phosphorylating agent.

In fact, to the extent of our knowledge, disphosphates of catecholamines are not reported in literature.

The only example of diphosphorylation of a compound structurally correlated with the catecholamines is the one described in U.S. Pat. No. 3,132,171 (Strong Cobb Arner Inc.) which describes, in particular, the diphosphorylation of DOPA with polyphosphoric acid. Nevertheless it is important to remark how our attempts to repeat the diphosphorylation procedure described in the aforesaid patent (particularly in the example 1) have substantially brought forth the formation of a mixture of monophosphorylation products.

Now we have surprisingly found that the diphosphates of catecholamines may be prepared in suitable conditions of phosphorylation and that the diphosphates of catecholamines show not only the same pharmacokinetic advantages of the monophosphates in comparison with the corresponding catecholamines but show further pharmacologically advantageous characteristics that make them particularly useful in the therapy.

Object of the present invention are thus the compounds of formula

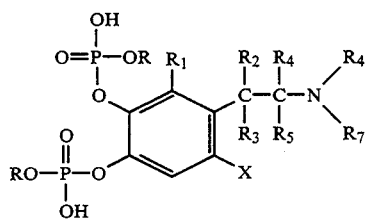

(I)

wherein

R is hydrogen, phenyl, phenylalkyl or a $C_1$–$C_6$ alkyl optionally substituted by hydroxy, alkoxy, acyloxy, amino, carboxy or alkoxycarbonyl groups;

$R_1$ is hydrogen, halogen, alkyl, alkoxy or, together with $R_3$ or $R_5$, has the meanings indicated below;

X is hydrogen or, together with $R_3$ or $R_5$, has the meanings indicated below;

$R_2$ is hydrogen or hydroxy;

$R_3$ is hydrogen or, together with $R_1$ or X, constitutes a chain of methylenes forming a ring having from 5 to 8 members;

$R_4$ is hydrogen, alkyl or alkoxycarbonyl;

$R_5$ is hydrogen, alkyl or, together with $R_1$ or X, constitutes a chain of methylenes forming a ring having from 5 to 8 members;

$R_6$ is hydrogen, allyl, acyl deriving from a natural aminoacid, $C_1$–$C_6$ alkyl optionally substituted by phenyl, 4- hydroxyphenyl or by a phenylalkylamino or phenoxyalkylamino group having from 1 to 3 carbon atoms in the alkyl moiety and optionally substituted on the phenyl;

$R_7$ is hydrogen or a $C_1$–$C_6$ alkyl; and their pharmaceutically acceptable salts.

When not otherwise specified, among the meanings for the substitutents in the general formula I, we refer: by alkyl, a straight or branched $C_1$–$C_4$ alkyl, by alkoxy, a straight or branched $C_1$–$C_4$ alkoxy, by acyloxy, an alkylcarbonyloxy having from 1 to 4 carbon atoms in the alkyl moiety, by halogen, a fluorine, chlorine, bromine or iodine atom.

Preferred compounds of formula I are the compounds wherein R is hydrogen, benzyl or a $C_1$–$C_4$ alkyl optionally substituted by a $C_1$–$C_4$ alkoxy group or by an acyloxy group; $R_1$ is hydrogen, halogen or, together with $R_3$ or $R_5$, has the meanings indicated below; X is hydrogen or, together with $R_3$ or $R_5$, has the meanings indicated below; $R_2$ is hydrogen or hydroxy; $R_3$ is hydrogen or, together with $R_1$ or X, forms a 6 carbon atoms ring; $R_4$ is hydrogen or methyl; $R_5$ is hydrogen or, together with $R_1$ or X, forms a 6 carbon atoms ring; $R_6$ is hydrogen, acyl deriving from glutamic acid or alanine, $C_1$–$C_6$ alkyl optionally substituted by 4-hydroxyphenyl, by a phenylalkylamino or phenoxyalkylamino group having two carbon atoms in the alkyl moiety, optionally substituted on the phenyl; $R_7$ is hydrogen or $C_1$–$C_4$ alkyl.

Still more preferred compounds or formula I are the compounds wherein R is hydrogen; $R_1$ is hydrogen, halogen or, together with $R_3$ or $R_5$, has the meanings indicated below; X is hydrogen or, together with $R_3$ or $R_5$, has the meanings indicated below; $R_2$ is hydrogen or hydroxy; $R_3$ is hydrogen or, together with $R_1$ or X, forms a 6 carbon atoms ring; $R_4$ is hydrogen or methyl; $R_5$ is hydrogen or, together with $R_1$ or X, forms a 6 carbon atoms ring; $R_6$ is hydrogen, acyl deriving from glutamic acid or alanine, $C_1$–$C_6$ alkyl optionally substituted by 4-hydroxyphenyl, by a phenylalkylamino or phenoxyalkylamino group having two carbon atoms in the alkyl moiety, optionally substituted on the phenyl; $R_7$ is hydrogen or $C_1$–$C_4$ alkyl. Specific examples of the compounds of formula I are:

dopamine 3,4-O-di-(dihydrogenphosphate)
N-methyldopamine 3,4-O-di-(dihydrogenphosphate)
adrenaline 3,4-O-di-(dihydrogenphosphate)
noradrenaline 3,4-O-di-(dihydrogenphosphate)
7,8-dihydroxy-1-phenyl-2,3,4,5-tetrahydro-1H-3-benzoazepine-7,8-O-di-(dihydrogenphosphate)
N-methyldopamine 3,4-O-di-(ethylhydrogenphosphate)
N-methyldopamine 3,4-O-di-(2-methoxyethylhydrogenphosphate)
N-methyldopamine 3,4-O-di-(polyvaloyloxymethylhydrogenphosphate)
N,N-di-n.propyldopamine 3,4-O-dihydrogenphosphate)

N-t.butyl-noradrenaline 3,4-O-di-(dihydrogenphosphate)

1-(3,4,5-trimethoxybenzyl)-6,7-dihydroxy-1,2,3,4-tetrahydroisoquinoline 6,7-O-di-(dihydrogenphosphate)

dopamine 3,4-O-di-(ethylhydrogenphosphate)

7,8-dihydroxy-1-(4-hydroxyphenyl)-2,3,4,5-tetrahydro-1H-3-benzoazepine 7,8-O-di-(dihydrogenphosphate)

N-(gamma-glutamyl-alpha-ethyl ester)-dopamine 3,4-O-di-(dihydrogenphosphate)

N-alanyl-dopamine 3,4-O-di-(dihydrogenphosphate)

N-(3,4-dihydroxyphenylethyl)-N'-(2-phenylethyl)-hexan-1,6-diamine 3,4-O-di-(dihydrogenphosphate)

N-[3-(4-hydroxyphenyl)-1-methylpropyl]-dopamine 3,4-O-di-(ethylhydrogenphosphate)

N-[3-(4-hydroxyphenyl)-1-methylpropyl]-dopamine 3,4-O-di-(dihydrogenphosphate)

6-chloro-7,8-dihydroxy-1-(4-hydroxyphenyl)-2,3,4,5-tetrahydro-1H-3-benzoazepine 7,8-O-di-(dihydrogenphosphate)

N-(3,4-dihydroxyphenylethyl)-N'-(2-phenylethyl)-hexan-1,6-diamine 3,4-O-di-(ethylhydrogenphosphate)

1-(N,N-di-n.propylaminomethyl)-6,7-dihydroxy-1,2,3,4-tetrahydro-1-naphthalene 6,7-O-di-(dihydrogenphosphate)

2-amino-5,6-dihydroxy-1,2,3,4-tetrahydronaphthalene 5,6-O-di-(dihydrogenphosphate)

Pharmaceutically acceptable salts of the compounds of formula I are the salts with bases such as, for instance, sodium potassium, calcium and magnesium hydroxides, carbonates or bicarbonates, diethylamine, ethanolamine, dicyclohexylamine, trihydroxymethylaminomethane, lysine, glucamine and arginine.

The compounds of formula I may present asymmetric carbon atoms and thus may exist in the form of stereoisomers.

Object of the present invention are thus the compounds of formula I either in the form of stereoisomeric mixtures or in the form of single stereoisomers.

The compounds of formula I object of the invention show a better absorption and a greater effectiveness in comparison with the corresponding catecholamines. According to the starting catecholamines, that is to say if they stimulate in particular the dopaminergic or adrenergic receptors, the improvements of the activities are observed in different therapeutic fields. In fact, the compounds according to the present invention are useful, for instance, in the therapy of cardiovascular and renal diseases such as cardiac failure, renal failure and hypertension, in the therapy of bronchial asthma and in the therapy of ocular hypertension.

Moreover, we noticed that such compounds are chemically stable at acidic pH and from the evaluation of enzymatic hydrolysis data we observed that the corresponding monophosphates were obtained by hydrolysis of the diphosphates of formula I.

Therefore we realized that the diphosphates of the present invention, besides the other pharmacological advantages above mentioned, show also the advantage of carrying out a slow release into the organism of the corresponding catecholamine monophosphates, whose biological value is already known.

The compounds of formula I are prepared by direct diphosphorylation of the catecholamines of formula

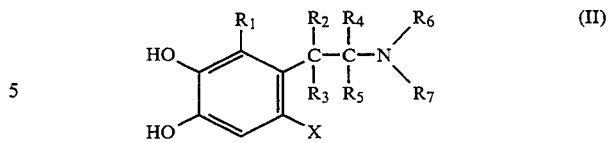

wherein $R_1$, $R_2$, $R_3$, $R_4$, $R_5$, $R_6$, $R_7$ and X have the meanings already indicated;
with a phosphorylating agent of formula

wherein
R' is phenyl, phenylalkyl or a $C_1$–$C_6$ alkyl optionally substituted by hydroxy, alkoxy, acyloxy, amino, carboxy or alkoxycarbonyl groups; in the presence of a strong base and in an inert organic solvent.

As phosphorylating agent a compound of formula III wherein R' is phenyl, benzyl or a $C_1$–$C_6$ alkyl is preferably used.

Still more preferably as phosphorylating agent is used a compound of formula III wherein R' is benzyl.

Examples of strong bases are hydrides, alkoxides or amides of alkaline or earth-alkaline metals.

Specific examples are sodium hydride, calcium hydride, sodium methoxide, sodium ethoxide, potassium t.butoxide and sodium amide. Sodium hydride is preferably used.

Specific examples of inert organic solvents are methylenechloride, tetrahydrofurane, ethyl acetate, dimethylformamide, pyridine and toluene or their mixtures.

From the diphosphorylation reaction of the catecholamines of formula II with the phosphorylating agent of formula III the compounds of formula

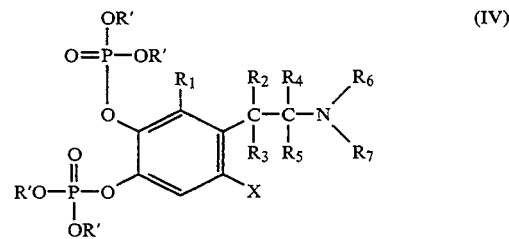

wherein R', $R_1$, $R_2$, $R_3$, $R_4$, $R_5$, $R_6$, $R_7$ and X have the meanings already indicated, are obtained.

At the end of the diphosphorylation reaction, one or both the R' radicals of each phosphate group of the compounds of formula IV, are removed.

Usually, when R' is a benzyl group, all the R' radicals are removed by hydrogenolysis obtaining in such a way the compounds of formula I wherein R is hydrogen.

When R' is other than benzyl instead, one of the R' radicals of each phosphate group only can be removed by hydrolysis obtaining the compounds of formula I wherein R is different from hydrogen.

Alternatively, the compounds of formula I wherein R is different from hydrogen may also be prepared from the corresponding compounds wherein R is hydrogen by esterification with a compound of formula

R'Z (V)

wherein R' has the meanings already indicated and Z is a suitable leaving group such as, for instance, halogen, preferably iodine, or an alkyl or arylsulfonyloxy, preferably methylsulfonyloxy, in the presence of a base and in a suitable aprotic organic solvent.

The process of direct diphosphorylation of the catecholamines of formula II is a further object of the invention.

It is clear that when carrying out the diphosphorylation of the compounds of formula II according to the process of the invention, it may be opportune to protect other functions optionally present in the compounds of formula II such as, for instance, primary or secondary amino functions or hydroxy functions other than the catechol hydroxy groups.

The protection may be carried out according to the conventional techniques by using, for instance, protecting groups such as benzyl, trityl or benzyloxycarbonyl which can be removed by hydrogenolysis or t.butoxycarbonyl, 1-adamantyloxycarbonyl, trifluoroacetyl, 3-fluorenylmethoxycarbonyl or 1,1-dimethylcyanoethoxycarbonyl which can be removed by hydrolysis.

A further form of protection that may result advantageous in the case of hydroxy aliphatic functions is that of carrying out the diphosphorylation on the corresponding ketoderivative, restoring then the hydroxy function by reduction.

It is important to remark how the process conditions of phosphorylation object of the invention are peculiar in such a way that allow to obtain, practically as a single product of phosphorylation, the catecholamine diphosphates of formula IV.

In fact by working in different conditions, particularly by using fully conventional phosphorylating agents such as orthophosphoric acid, pyrophosphoric acid, phosphorus pentoxide, polyphosphoric acid, chlorophosphoric acid, phosphoryl chloride or phosphoryl bromide, a mixture of the two monophosphorylated isomers of the catecholamine of formula II is obtained.

The activity of the compounds of formula I has been evaluated in comparison with the corresponding monophosphates described in European patent No. 0 167 204.

For example, the activity of N-methyldopamine 3,4-O-di-(dihydrogenphosphate) on cardiovascular parameters in anesthetized dog has been compared with that of N-methyldopamine 4-O-dihydrogenphosphate.

Both the substances showed to be able to reduce significantly the vascular renal resistance and to increase renal blood flow.

Nevertheless, the activity of N-methyldopamine 3,4-O-di-(dihydrogenphosphate) becomes evident at molar doses lower than those of N-methyldopamine 4-O-dihydrogenphosphate.

These properties are particularly useful in therapy.

The compounds object of the present invention may be administered in association with other drugs which are compatible with them and develop a complementary action.

For therapeutical applications, the compounds of formula I may be administered in the form of suitable pharmaceutical compositions. These pharmaceutical compositions, which are a further object of the present invention, contain a therapeutically effective amount of one or more compounds according to the invention in admixture with a suitable carrier.

Suitable carriers are constituted by one or more solid or liquid excipients for pharmaceutical use.

The compositions object of the invention may be suitable for oral, rectal, parenteral or topical administration and, for instance, may be in the form of tablets, pills, capsules, solutions, suspensions or emulsions.

The pharmaceutical compositions object of the invention are prepared according to conventional techniques.

In order to better illustrate the present invention the following examples are now given.

EXAMPLE 1

Preparation of N-benzyloxycarbonyldopamine 3,4-O-di-(dibenzylphosphate)

A suspension of 55% NaH in mineral oil (9.6 g; 0.22 mols) was added to a solution of N-benzyloxycarbonyldopamine (28.7 g; 0.1 mols) in dimethylformamide (290 ml).

After 1 hour at room temperature, a solution of dibenzylphosphohydrochloride (65.23 g; 0.22 mols) in toluene (650 ml) was added dropwise.

After 1 hour more a mixture of acetic acid (10 ml) and water (10 ml) was added therein. The solution was washed with water, dried over $Na_2SO_4$, filtered off and evaporated. The residual oil was washed with petroleum ether and purified by chromatography on a silica gel column (eluent: $CH_2Cl_2$ with increasing quantities up to 2% of methanol) obtaining N-benzyloxycarbonyldopamine 3,4-O-di-(dibenzylphosphate) in oily form (75 g; yield 93%).

$^1$N-NMR (300 MHz, $CDCl_3$): δ (ppm): 2.61 (t, 2H); 3.24 (quartet, 2H); 5.06–5.12 (m, 10H); 6.87 (d, 1H); 7.01 (s, 1H); 7.22–7.35 (m, 26H).

By working in a similar way the following compounds were prepared:

N-benzyloxycarbonyl-N-methyldopamine 3,4-O-di-(dibenzylphosphate) in oily form $^1$N-NMR (300 MHz, $CDCl_3$): δ (ppm): 2.72 (m, 2H); 2.84 (d, 3H); 3.49 (quartet, 2H); 5.06–5.12 (m, 10H); 6.88 (dd, 1H); 7.14 (d, 1H); 7.22–7.45 (m, 26H).

N,N-di-n-propyldopamine 3,4-O-di-(dibenzylphosphate) in oily form $^1$N-NMR (300 MHz, $CDCl_3$): δ (ppm): 0.98 (t, 6H); 1.39–1.51 (m, 4H); 2.37–2.43 (m, 4H); 2.66–2.77 (m, 4H); 5.07–5.11 (m, 8H); 6.91 (dd, 1H); 7.15 (d, 1H); 7.22–7.30 (m, 21H).

N-benzyloxycarbonyl-2(S)-amino-5,6-dihydroxy-1,2,3,4-tetrahydronaphthalene 5,6-O-di-(dibenzylphosphate) in oily form $^1$N-NMR (300 MHz, $CDCl_3$): δ (ppm): 1.65 (m, 1H); 1.95 (m, 1H); 2.60 (m, 1H); 2.83 (m, 2H); 3.04 (m, 1H); 3.97 (m, 1H); 5.09 (m, 10H); 6.81 (d, 1H); 7.17–7.38 (m, 26H).

N-benzyloxycarbonyl-L-dopa ethyl ester 3,4-D-di-(dibenzylphosphate) in oily form $^1$N-NMR (300 MHz, $CDCl_3$): δ (ppm): 1.20 (t, 3H); 2.96–3.10 (m, 2H); 4.16 (quartet, 2H); 4.58 (dd, 1H); 5.05–5.09 (m, 10H); 6.84 (dd, 1H); 7.12 (d, 1H); 7.21–7.38 (m, 26H).

N-t.butylnoradrenaline 3,4-O-di-(dibenzylphosphate) in oily form

Mass spectrum (Thermospray) m/e: 746.9 ($M^+ + 1$).

N-benzyloxycarbonylnoradrenalone 3,4-O-di-(dibenzylphosphate) in oily form $^1$N-NMR (300 MHz, $CDCl_3$): δ (ppm): 3.55 (d, 2H); 5.08–5.18 (m, 10H); 7.22–7.43 (m, 26H); 7.65 (d, 1H); 7.78 (s, 1H).

EXAMPLE 2

Preparation of dopamine 3,4-O-di-(dihydrogenphosphate) (Compound 1)

10% Pd supported on charcoal containing 50% of water (7 g) was added to a solution of N-benzyloxycarbonyldopamine 3,4-O-di-(dibenzylphosphate) (35 g; 43.3 mmols), prepared as described in example 1, in 80% ethanol (350 ml).

The mixture was hydrogenated into Parr apparatus.

When the hydrogen absorption was over, the catalyst was filtered off, washed with 80% ethanol first and then with water. The collected solutions were concentrated under vacuum on a steam bath at about 40° C.; the residue was collected with 96% ethanol and filtered. After drying the compound 1 (10.8 g; yield 80%) was obtained.

M.p. 174°–178° C.

$^1$N-NMR (300 MHz, D$_2$O): δ (ppm): 2.98 (t, 2H); 3.29 (t, 2H); 7.07 (dd, 1H); 7.26 (d, 1H); 7.32 (d, 1H).

Mass spectrum (Thermospray) m/e: 312 (M$^+$-H), 232 (M$^+$-PO$_3$H)

By working in a similar way the following compounds were prepared:

N-methyldopamine 3,4-O-di-(dihydrogenphosphate) (Compound 2)

M.p. 169°–173° C.

$^1$N-NMR (300 MHz, D$_2$O): δ (ppm): 2.68 (s, 3H); 2.99 (t, 2H); 3.31 (t, 2H); 7.06 (dd, 1H); 7.26 (d, 1H); 7.32 (d, 1H).

Mass spectrum (Thermospray) m/e: 326 (M$^+$-H)

N,N-di-n-propyldopamine 3,4-O-di-(dihydrogenphosphate)

M.p. 218°–220° C.

$^1$H-NMR (300 MHz, D$_2$O/NaHCO$_3$): δ (ppm): 0.98 (t, 6H); 1.68–1.82 (m, 4H); 3.04 (t, 2H); 3.14–3.20 (m, 4H); 3.46 (t, 2H); 6.96 (dd, 1H); 7.33–7.36 (m, 2H).

2(S)-amino-5,6-dihydroxy-1,2,3,4-tetrahydronaphthalene 5,6-O-di-(dihydrogenphosphate) (Compound 3)

M.p. 153°–156° C.

$^1$N-NMR (300 MHz, D$_2$O): δ (ppm): 1.83–1.96 (m, 1H); 2.14–2.24 (m, 1H); 2.78–2.85 (m, 2H); 3.00–3.13 (m, 2H); 4.05–4.15 (m, 1H); 6.90 (d, 1H); 7.18 (d, 1H).

L-Dopa ethyl ester 3,4-O-di-(dihydrogenphosphate) (Compound 4)

$^1$N-NMR (300 MHz, D$_2$O): δ (ppm): 1.27 (2 triplet, 3H); 3.02–3.38 (m, 2H; 4.30 (2 quartet, 2H); 4.35–4.42 (m, 1H); 7.03 (dd, 1H); 7.24 (d, 1H); 7.32 (d, 1H).

N-t.butyl-noradrenaline 3,4-O-di-(dihydrogenphosphate) (Compound 5)

$^1$N-NMR (300 MHz, D$_2$O): δ (ppm): 1.37 (s, 9H); 3.20–3.36 (m, 2H); 4.85 (dd, 1H); 7.19 (dd, 1H); 7.36–7.38 (m, 1H).

Noradrenaline 3,4-O-di-(dihydrogenphosphate) (Compound 6)

$^1$N-NMR (300 MHz, D$_2$O): δ (ppm): 3.18–3.34 (m, 2H); 4.97 (dd, 1H); 7.18 (d, 1H); 7.35–7.38 (m, 2H).

EXAMPLE 3

Preparation of dicyclohexylamine salt of N-(N-benzyloxycarbonyl-L-alanyl)-dopamine 3,4-O-di-(dihydrogenphosphate)

A suspension of N-benzyloxycarbonyl-L-alanine N-hydroxysuccinimide ester (3.84 g; 12 mmols) in absolute ethanol (30 ml) was added to a solution of dopamine 3,4-O-di-(dihydrogenphosphate) (3.13 g; 10 mmols), prepared as described in example 2, and dicyclohexylamine (7.96 ml; 40 mmols) in 50% ethanol (60 ml).

After 1 hour under stirring, the solution became homogeneous and CH$_2$Cl$_2$ (120 ml) was added.

The phases were separated and the organic layer was washed with water, with a 1% solution of NaHCO$_3$, with a 10% solution of KHSO$_4$ (40.8 ml; 30 mmols) and finally with water again. After drying over sodium sulfate and evaporation of the solvent, the residue was purified by chromatography on a silica gel column (eluent: CH$_2$Cl$_2$:CH$_3$OH:H$_2$O=84:15:1) obtaining dicyclohexylamine salt of N-(N-benzyloxycarbonyl-L-alanyl)-dopamine 3,4-O-di-(dihydrogenphosphate) (43 g; yield 49%) as oil.

$^1$H-NMR (300 MHz, DMSO-d$_6$): δ (ppm): 4.97–5.09 (m, 2H); 6.75 (d, 1H); 7.03–7.08 (m, 2H); 7.28–7.46 (m, 5H). The signals of dicyclohexylamine covered those of the aliphatic moiety of the product.

By working in a similar way but using the alpha-ethyl ester gamma N-hydroxysuccinimido ester of the N-benzyloxycarbonyl-L-glutamic acid the following compound was prepared:

dicyclohexylamine salt of N-(N-benzyloxycarbonyl-gamma-glutamyl-alpha-ethyl ester)-dopamine 3,4-O-di-(dihydrogenphosphate) in oily form.

EXAMPLE 4

Preparation of magnesium salt of N-L-alanyldopamine 3,4-O-di-(dihydrogenphosphate) (Compound 7)

10% Pd supported over charcoal containing 50% of water (1.2 g) was added to a solution of N-(N-benzyloxycarbonyl-L-alanyl)-dopamine 3,4-O-di-(dihydrogenphosphate) (6 g; 6.8 mmoles), prepared as described in example 3, in absolute ethanol (60 ml).

The mixture was catalytically hydrogenated until hydrogen absorption was over. After filtration and evaporation of the solvent under vacuum, the residue was dissolved in methanol and (CH$_3$COO)$_2$Mg.4 H$_2$O (1.46 g; 6.8 mmols) dissolved in methanol was added. The precipitated salt was first filtered and washed with methanol and ether, then after drying, was resuspended in 96% ethanol. After filtration and drying under vacuum, the compound 7 (1.2 g; yield 41%) was obtained.

$^1$N-NMR (300 MHz, D$_2$O): δ (ppm): 1.38 (d, 3H); 2.69–2.85 (m, 2H); 3.35–3.65 (m, 2H); 3.65 (quartet, 1H); 6.96 (d, 1H); 7.25 (d, 1H); 7.31 (d, 1H).

By working in a similar way the following compound was prepared:

dicyclohexylamine salt of N-(gamma-glutamyl-alpha-ethyl ester)-dopamine 3,4-O-di-(dihydrogenphosphate) (Compound 8)

$^1$N-NMR (300 MHz, D$_2$O): δ (ppm): 2.92–3.02 (m, 2H); 3.20–3.28 (m, 2H); 4.19 (quartet, 2H); 6.72 (d, 1H); 6.98 (d, 1H); 7.03 (d, 1H).

The signals of dicyclohexylamine covered those at higher fields of the aliphatic moiety of the product.

COMPARATIVE EXAMPLE 1

Repetition of the example 1 according to U.S. Pat. No. 3,132,171

The procedure reported in example 1 of U.S. Pat. No. 3,132,171 was exactly repeated.

By cooling the reaction mixture after 1 hour, as described, a HPLC analysis of the reaction mixture gave the following results:

L-DOPA: 0.56% by weight

L-DOPA 3-O-mono-(dihydrogenphosphate): 38.13% by weight

L-DOPA 4-O-mono-(dihydrogenphosphate): 40.26% by weight

L-DOPA 3,4-O-di-(dihydrogenphosphate): 10.14% by weight

Non-identified degradation products: 10.91% by weight

We claim:

1. A compound of formula

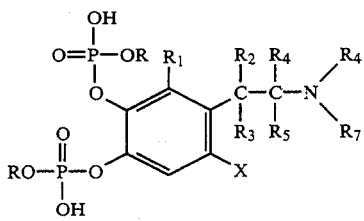 (I)

wherein

R is hydrogen, phenyl, phenylalkyl or a $C_1$–$C_6$ alkyl optionally substituted by hydroxy, alkoxy, acyloxy, amino, carboxy or alkoxycarbonyl groups;

$R_1$ is hydrogen, halogen, alkyl, alkoxy or, together with $R_3$ or $R_5$, has the meanings indicated below;

X is hydrogen or, together with $R_3$ or $R_5$, has the meanings indicated below;

$R_2$ is hydrogen or hydroxy;

$R_3$ is hydrogen or, together with $R_1$ or X, constitutes a chain of methylenes forming a ring having from 5 to 8 members;

$R_4$ is hydrogen, alkyl or alkoxycarbonyl;

$R_5$ is hydrogen, alkyl or, together with $R_1$ or X, constitutes a chain of methylenes forming a ring having from 5 to 8 members;

$R_6$ is hydrogen, allyl, acyl deriving from a natural aminoacid, $C_1$–$C_6$ alkyl optionally substituted by phenyl, 4- hydroxyphenyl or by a phenylalkylamino or phenoxyalkylamino group having from 1 to 3 carbon atoms in the alkyl moiety and optionally substituted on the phenyl;

$R_7$ is hydrogen or a $C_1$–$C_6$ alkyl;

and its pharmaceutically acceptable salts.

2. A compound according to claim 1, wherein R is hydrogen, benzyl or a $C_1$–$C_4$ alkyl optionally substituted by a $C_1$–$C_4$ alkoxy group or by an acyloxy group; $R_1$ is hydrogen, halogen or, together with $R_3$ or $R_5$, has the meanings indicated below; X is hydrogen or, together with $R_3$ or $R_5$, has the meanings indicated below; $R_2$ is hydrogen or hydroxy; $R_3$ is hydrogen or, together with $R_1$ or X, forms a 6 carbon atoms ring; $R_4$ is hydrogen or methyl; $R_5$ is hydrogen or, together with $R_1$ or X, forms a 6 carbon atoms ring; $R_6$ is hydrogen, acyl deriving from glutamic acid or alanine, $C_1$–$C_6$ alkyl optionally substituted by 4-hydroxyphenyl, by a phenylalkylamino or phenoxyalkylamino group having two carbon atoms in the alkyl moiety, optionally substituted on the phenyl; $R_7$ is hydrogen or $C_1$–$C_4$ alkyl.

3. A pharmaceutical composition comprising one or more compounds according to claim 1, optionally in admixture with one or more excipients suitable for pharmaceutical use.

4. N-methyldopamine 3,4-O-di(di-hydrogenphosphate).

* * * * *